(12) United States Patent
Talluri

(10) Patent No.: US 10,460,450 B2
(45) Date of Patent: Oct. 29, 2019

(54) METHOD FOR ESTIMATING THE FAT MASS OF A SUBJECT THROUGH DIGITAL IMAGES

(71) Applicant: Antonio Talluri, Bagno a Ripoli (IT)

(72) Inventor: Antonio Talluri, Bagno a Ripoli (IT)

( * ) Notice: Subject to any disclaimer, the term of this patent is extended or adjusted under 35 U.S.C. 154(b) by 66 days.

(21) Appl. No.: 15/571,842

(22) PCT Filed: Mar. 1, 2016

(86) PCT No.: PCT/IB2016/051118
§ 371 (c)(1),
(2) Date: Feb. 6, 2018

(87) PCT Pub. No.: WO2016/189400
PCT Pub. Date: Dec. 1, 2016

(65) Prior Publication Data
US 2018/0300883 A1 Oct. 18, 2018

(30) Foreign Application Priority Data

May 26, 2015 (EP) ..................................... 15425037

(51) Int. Cl.
| | |
|---|---|
| *G06T 7/194* | (2017.01) |
| *H04N 5/262* | (2006.01) |
| *G06T 11/60* | (2006.01) |
| *G06T 7/90* | (2017.01) |
| *G16H 30/40* | (2018.01) |
| *G06T 7/62* | (2017.01) |
| *A61B 5/00* | (2006.01) |

(Continued)

(52) U.S. Cl.
CPC ............ *G06T 7/194* (2017.01); *A61B 5/0077* (2013.01); *A61B 5/4872* (2013.01); *G06T 7/0012* (2013.01); *G06T 7/62* (2017.01); *G06T 7/90* (2017.01); *G06T 11/60* (2013.01); *G16H 30/40* (2018.01); *H04N 5/2621* (2013.01); *A61B 2560/0487* (2013.01); *G06T 2207/30196* (2013.01); *H04L 67/10* (2013.01)

(58) Field of Classification Search
None
See application file for complete search history.

(56) References Cited

U.S. PATENT DOCUMENTS

2014/0031700 A1* 1/2014 Ferrantelli ........... A61B 5/1072
600/476

FOREIGN PATENT DOCUMENTS

| WO | 2008147888 | 12/2008 |
|---|---|---|
| WO | 20120079014 | 6/2012 |

OTHER PUBLICATIONS

Deshpande, "Estimation of Body Mass Distribution Using Projective Image," Jan. 2013 (Year: 2013).*

(Continued)

*Primary Examiner* — Christopher Braniff
(74) *Attorney, Agent, or Firm* — Themis Law

(57) ABSTRACT

A method for determining the fat mass of a subject includes the steps of acquiring an image of the subject through a digital device, and generating a virtual frame that contains at least in part that image. The virtual frame contains the subject, on the basis of its height or of the greater size in the case of animals, to provide an estimation of the content of the fat mass through an algorithm on the basis of at least an indicative index of the area occupied by the subject with respect to the area of the frame in which it is contained at least in part.

12 Claims, 6 Drawing Sheets

(51) Int. Cl.
*G06T 7/00* (2017.01)
*H04L 29/08* (2006.01)

(56) References Cited

OTHER PUBLICATIONS

Suhas Deshpande, Estimation of body mass distribution using projective image, Jan. 19, 2013, pp. 1-14.

* cited by examiner

METHOD FOR ESTIMATING THE FAT MASS OF A SUBJECT THROUGH DIGITAL IMAGES

TECHNICAL FIELD

The present invention refers to the technical field relative to the devices for determining one or more physiological parameters of a subject, both a human being and an animal in general.

In particular, the invention refers to a method that allows to estimate the quantity of fat mass contained in a body.

BACKGROUND ART

The determination of the fat mass is of relevant importance in many fields.

In the medical field, for example, the determination of the fat mass allows to diagnose and prevent and helps to plan eventual interventions aimed at both losing and putting on weight.

The determination of the fat mass can also be useful in animals, both alive and slaughtered, for instance for qualitative and evaluative purposes and for eventual subsequent slaughters.

The knowledge of the fat mass in a cut of meat, for example ham, can be useful to quantify the quality and/or the nutritional properties thereof.

In the known art, there exists an Italian patent by the same inventor of this now method and in the name of Akern S.r.l. under number 0001343130 entitled:

"A process for the determination of the density of a human body or other, and a device for realizing it".

The patent describes a methodology, with relative apparatus, that allows to determine the volume from which to obtain, in association with the weight, an estimation of the body density and from which it is possible to derive the content of fat mass (for example, of a person and also of a simple cut of meat already slaughtered).

The method foresees the use of one or two tele-cameras, the acquisition of at least two images and the use of a frame of a known size.

Basically, a location on which the subject (for example a person) is placed is foreseen.

The person is standing inside the frame and in front of a background of a white, not reflecting, homogeneous colour.

Two tele-cameras (or a single one when the person is placed on a rotating support whose rotation is governed by a micro-controller or the subject is capable of rotating, but with a monitored rotation of 90°) allow to acquire two images of the subject orthogonal between them and, in particular, a view with the subject placed frontally (anteroposterior projection) and a view with the subject placed abreast (latero-lateral projection).

The idea, therefore, consists in comparing the two areas (A1, A2) of the two profiles acquired on the basis of the concept that the area of the entire image delimited by a frame furnished with known sizes is in part "occupied" or filled in by the profiles taken and therefore, from here, it is possible to determine by proportionality a total body surface from which to derive also the estimation of the body volume.

Basically, once the two images are acquired, a software processes a comparison of colour of the pixels between background and profile in such a way as to distinguish the profile and obtain its area.

Once the two areas (A1, A2) are known, a specific formula obtains an estimation of the volume. Known the weight of the body under exam, the determination of the density is made as the relation between volume and weight and subsequently the estimation of the fat mass takes place.

The method described, though functioning, suffers from some technical inconveniences.

The apparatuses required are cumbersome and relatively expensive. In particular, a tele-camera is required, as well as a support base provided with a contour (frame) of a known size and sufficiently wide as to contain also subjects with big body masses and sufficiently high as to allow the sample under exam to be erect. If the support base is not of the assisted or anyway controlled rotation type, it is even necessary the use of two tele-cameras appropriately placed or it is necessary to obtain a rotation of the subject under exam of 90° as precise as possible, in such a way as to acquire images normal among them.

All this means an apparatus that is expensive and cumbersome, destined to specialized structures, and operated by operators appropriately trained, rendering the determination of the fat mass a check that is only feasible in specialized locations.

A further document is also known, available on the Internet with the title "Estimation of body mass distribution using projective image".

Such a document describes a method for determining a fat mass by using image acquisition. In particular, two images have to be acquired, that is a front one and a lateral one, as described on page 11 of such a document. Such an acquisition of two images is essential for being able to calculate the fat mass in accordance with the formula used that requires the knowledge of ovoid volumes.

A calibration in the two images takes place by inserting, in the image to be acquired, an object of known size, as described on page 8. In this manner, a correlation is obtained between one or more pixels and a unit of measure. The images are processed to eliminate any interference. Last, the images are processed converting them into a greyscale, as described on page 12, in such a way as to calculate a volume. The volume, as described on page 13, is calculated by creating about fifty transversal sections of the subject in the two images and measuring the height (h) and the length (a, b) of each section. In this manner, the surface of each ovoid section (elliptical section) can be calculated and, as a consequence, the overall volume can be obtained as the sum of all the volumes calculated.

Such a method presents many technical inconveniences.

First of all, it is necessary to acquire two images to have a volume. Consequently, the processing of the images and the consequent calculation results to be heavier.

The processing described takes place through Matlab, which is a complex and expensive programme. Moreover, the calculation formula used renders obligatory not only the acquisition of two images but also the determination of the correlation between pixel and a real unity of measure to obtain a body volume that has to be necessarily precise. Only in this way is it possible to determine the essential density thereof to apply the formulas of Siri and of Brozek to obtain the body composition. This renders the procedure even more difficult.

DISCLOSURE OF INVENTION

It is therefore the aim of the present invention to provide an innovative method that solves said technical inconveniences.

It is therefore the aim of the present invention to provide a method that allows to estimate the content of fat mass in a simple way (of the "do it yourself" type), without requiring particular, complex and cumbersome apparatuses, and rendering said determination of measurement accessible to anyone, without the need for addressing a specialized structure, so even allowing an individual (personal, home) management.

In particular, it is the aim of the present invention to provide a method in which the acquisition of a single image is enough, making a calculation that does not necessarily require a dimensional correlation between pixel and a unity of measure through the use of external objects of reference, the whole simplifying such a method from the procedural point of view.

Those and other aims are reached with a method for the determination of the fat mass of a subject, in accordance with claim 1.

Such a method comprises the operations of:

Acquisition of at least one image containing a background and a subject (2) through a digital device (1);

Generation of a virtual frame (A, A', B', B) that contains at least a part of said subject (2) in the image, in particular a significant part of said subject;

The virtual frame (A, A', B, B') generated comprises two horizontal lines (A-A', B-B'), parallel one to the other, having a distance between them to which is attributed a value correlated to the height (h) value of the subject shown, preferably exactly the height value of the subject, and two vertical lines (A-B, A-B'), parallel one to the other, having a distance between them to which is attributed a value correlated as well to the height (h) value of the subject shown, in particular one fraction of the height h, preferably 0.4 h.

In this way, the area S of the frame is obtained as the product of the base and the height.

Determination of the content of fat mass through an algorithm on the basis of at least an indicative index of the area (A_1) occupied by the subject (2) in the image, with respect to the area (B_1) of the frame in which, such an area (A_1) results to be contained at least in part.

The subject inserts his height h and the software generates the frame that contains at least one significant part of the subject to calculate said index, attributing to the vertical lines such a height value (or a function thereof).

The distance between the vertical lines, that is the interaxis thereof, is also a value pre-fixed by the software, preferably one fraction of the height. The height (h) is inserted in the software by the user.

Thus, it s possible to determine by default the surface (B_1) of the virtual frame in an immediate way as the product of the base (known since pre-fixed, generally as one fraction of h) and the height (known since assumed as the value h inserted by the user).

The area A_1 of the subject is obtained, for example, by calculating the proportion of pixels that compose the background, and whose surface (B_1) is known, and the pixels that compose the image.

Preferably, even if different formulas result to be usable, the present invention in the preferred embodiment of the invention uses a mathematical regression comparing the indicative index calculated, of occupied surface, and associating it to the age, the sex, the height and the weight versus a dependent variable (fat mass) obtained with a reference method that has long been used (DEXA, Plicometry, Bio-electrical impedance analysis BIA-Densitometry). In this way, above all, estimation errors are avoided inherent to the use of formulas with volumes that do not take into account that the estimation of the density is rendered imprecise by the several cavities containing air present in the human body and that alter the result deriving from the weight/volume relation.

In that way, all said inconveniences are solved.

With respect to document 00C1343130 in the name of Akern, the generation of the virtual frame avoids and substitutes the presence of cumbersome and expensive bases of support and on which to place the subject and relative structural frames.

With respect to the document found on the Internet, there is the advantage that the acquisition of a single image is enough. In particular, the virtual frame, being derived from the height (h) of the subject, permits to calculate a relation between area of the subject and area of the frame itself as an indicative of the volume anyway usable according to regression formulas. In this manner, a single image, preferably lateral (sagittal plane), is enough to compute an estimation of the fat mass in a sufficiently precise way, eventually with mathematical regression methods versus reference methods.

In the document of known art cited, on the contrary, a frame correlated with the height of the subject is not either discussed or used and, for this reason, the calculation of fat mass requires, above all, the calibration of the image, and further the use of two images, normal between them, to obtain ovoid sections and therefore an overall volume.

The use of the virtual frame correlated with the height of the subject does not require the use or the insertion inside the picture of a reference object to create a correlation between a pixel and a real unity of measure since, now, a dimensionless index is used. On the contrary, in such a document of known art it is shown that a reference object has to be used idoneous to obtain real measures essential for the calculation of the volume and of the density, complicating the process.

In addition, the image can also be acquired through, for example, mobile phones, Tablets, I-phones, smartphones, etc., which, being furnished with photo-cameras and microprocessors, can themselves be capable of acquiring the image and generating such a virtual frame and operate said calculation in any place that is sufficiently adequate.

The whole significantly simplifies the necessary apparatuses from the structural and operative points of view.

To attribute to the frame a height value that coincides with the height of the subject allows to use any image acquired at any distance. It means it is no longer necessary to acquire images always at the same distance from the objective. In the calculation of the fat mass there intervenes the knowledge of the relation between area occupied by the subject in the frame and area of the frame itself. Although it is a dimensionless measure, such a relation has to be subsequently dimensioned to a coherent measure of the subject shown and this is possible precisely thanks to the fact that said frame of calculation has a length that is correlated to the height of the subject of which the measure wants to be taken.

Further advantages can be deduced from the dependent claims.

BRIEF DESCRIPTION OF DRAWINGS

Further features and advantages of the present device, and relative method as per the invention, will result to be clearer with the description that follows of one of its embodiments, made to illustrate but not to limit, with reference to the annexed drawings, wherein:

FIG. 3 shows the image enlarged and cut out, while

DESCRIPTION OF SOME PREFERRED EMBODIMENTS

Figure 1:
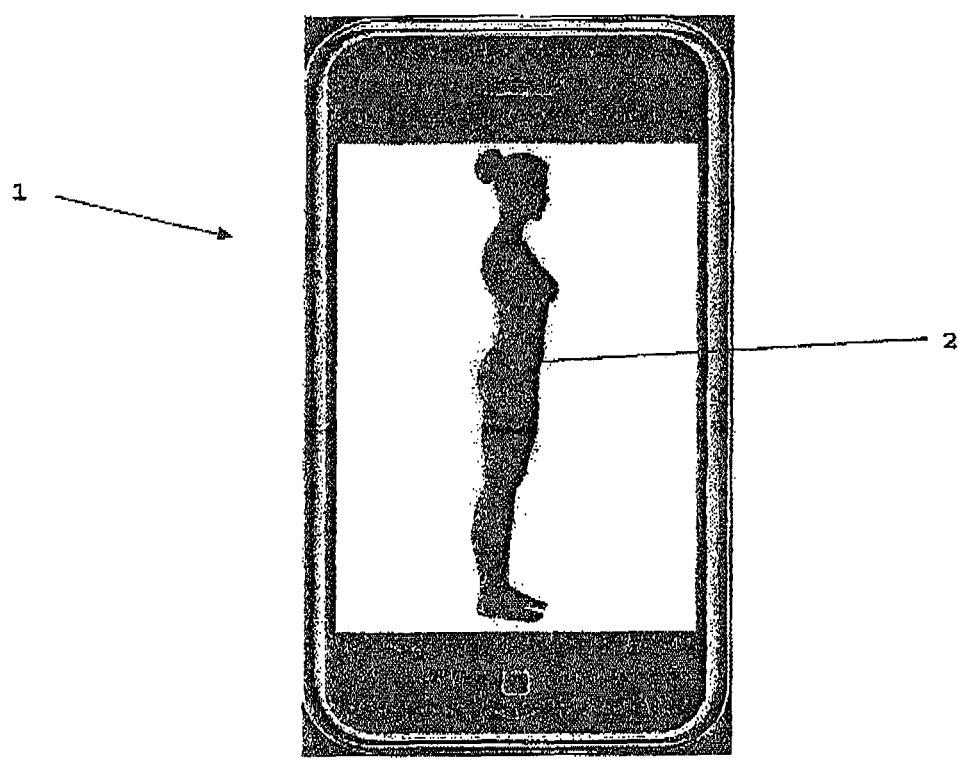
FIG. 1 shows a mobile telephony device of the I-phone or Smartphone type (or equivalently a device of the Tablet type) through which it is possible to acquire a sagittal image (in jargon called latero-lateral) of a subject placed abreast.

FIG. 1 it is represented, in accordance with the invention, a mobile telephony device 1, for example of the I-Phone or Smart-Phone type or a portable device provided with photo-camera and Wi-Fi connection of the Tablet, portable PC and the like type.

Such devices, above all those of mobile telephony (of relatively recent diffusion) have become of common use and are more and more substituting old mobile phones with more limited functions.

In fact, they have much more powerful processors, therefore resulting to be small portable PCs capable of making many more operations with respect to a classic mobile phone. In particular, apart from allowing the normal calling and the sending of messages, they are provided with Internet connection and, in an easy and quick way, allow to surf the Internet. Applications (called in technical jargon with the "App" acronym) are always more diffused, many of which are downloadable also free of charge, and that allow, once downloaded, to make multiple operations that are implemented through the processor of the mobile phone in which they have been installed.

There exist applications in all fields that go from entertainment to work and usefulness in general.

The present invention, which is described in detail below, can for example be implemented in the form of an "App" that is compatible with the operative systems diffused (Apple, Android, Windows, etc.), downloadable on the mobile telephony device or Tablet, and that will be described in detail below.

Alternatively, it is obviously possible to foresee a mobile telephony device that includes a memory chip (for example, an SD card) or a processor already programmed to function in accordance with the present invention (therefore without the need for downloading a specific application).

In a further alternative, as clarified below, a part at the operation is implemented by the mobile telephony device or by the device that can be connected to the Internet, which subsequently sends certain information to a dedicated system put on the Internet or in a more recent system called "cloud" which carries out the rest of the operations.

Having said that, FIG. 1 represents a mobile telephony device 1 (or, as said, a mobile device) that frames the silhouette of a subject.

Unlike the cited known art, the acquisition of the image now takes place through a mobile telephony device, or anyway a digital device in general of the portable type, which integrates in sé a processor and a user interface system (for example, a touch screen) capable of processing, modifying or touching up the images and making all the subsequent calculations, among which also an eventual sending via the Internet also of the single non processed picture to a "cloud" system to obtain a service that can comprise, apart from the calculation of fat mass, also eventual expert advice, favouring the remote follow-up at a low cost.

The image can also be taken with a tele-camera or another device and then sent or loaded, for example, to the mobile telephony device on which such an application is foreseen.

All this simplifies significantly the procedure of the known art since the specific tele-cameras on tripod, and above all the cumbersome contour structures, are not necessary anymore. It is not necessary anymore either to transfer the information of the image acquired with the tele-camera to an external processor.

Through the use of a completely normal mobile telephony device the user can, in a simple mould quick way, check autonomously, under any circumstances and in any environment an estimation of the body fat mass.

Each subject can therefore obtain at any moment and in any place a simple and quick measurement.

Having said that, and going further into the descriptive detail of the invention, the mobile telephony device 1 acquires an image 2 of a subject. The image contains a background and the subject shown.

The subject, preferably, has to wear a bathing suit or only underwear or an adherent suit, rendering well visible the profile of his own body.

In such a manner, all his body will be characterizable by an image with pixels of colours very close one to the other or well identifiable on the basis of the colour and/or brightness.

Moreover, the subject, preferably, has to be placed in a lateral position with the arms that run along the trunk to permit the acquisition of an image of the full-body sagittal profile.

The background for the acquisition of the image has to be, preferably, of an idoneous colour to create a contrast with the colour of the subject, for example white and, more preferably, not reflecting (opaque), in such a way as to result to be a net contrast between the image acquired and the background and possibly avoiding that the background creates reflexes.

For example, a simple wall of a room, generally white or clear, can be used.

It is possible to foresee, optionally, an suitability analysis of the background by simply acquiring in the first place an image of the single background, to check through digital conditioning if it contains disturbances or if it falls within a certain percentage of homogeneity. It is enough to scan the image that shows the single background and check, for example, the threshold of colour of the pixels that compose it to determine if they fall within a range of pre-established homogeneity or not. In case a certain number at pixels does not fall within, exceeding on the whole the range of pre-established homogeneity, a notice can be foreseen that asks for the selection of a more adequate background for the purpose.

An eventual interpolation, easily realizable (for example, not limiting through curves of Bézier), can also complete the discontinuity created by the eventual section of the body covered by the bathing suit or the underwear.

Figure 2:
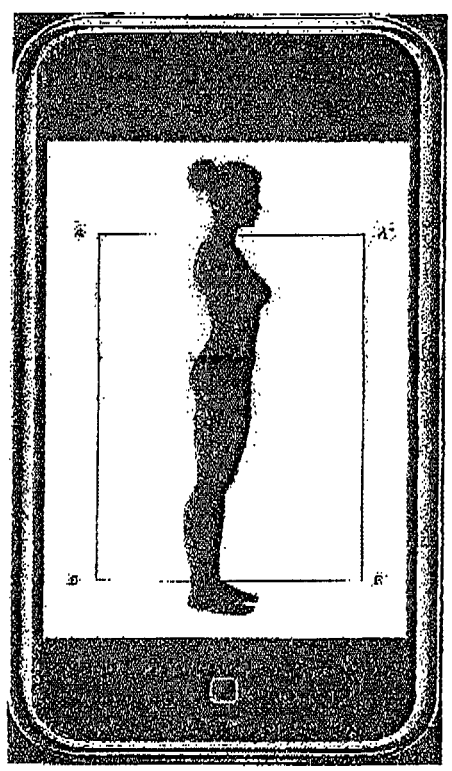
FIG. 2 shows how the specific application (software) that is furnished allows to cut out the image with appropriate frame.

Having said that, in a first preferred embodiment of the invention, as shown in FIG. 1 and in FIG. 2, the acquisition of a single image is enough in which the subject is placed in a lateral position, normal to the objective (to obtain images re-coloured digitally as per FIG. 1 and FIG. 2) or front position and always normal to the objective.

The software, implemented in the mobile device, for example, through a specific "App", requests the insertion of same data, among which the height (h) of the subject and the weight (p) of the subject.

The data (as said, weight and height but also other eventual data such as age, sex, level of physical activity, etc.) can be requested and be inserted before or after the acquisition of the image.

The insertion of the height (h) allows to generate two horizontal lines (A-A', B-B') spaced between them on the basis of said height (h) and to obtain then a frame in which at least in part the silhouette portrayed is contained, as per FIG. 2.

The insertion of the datum height allows to correlate the frame with the figure under exam and from here, to obtain a plausible value of fat mass.

In particular, the two horizontal lines (A-A') and (B-B'), once displayed on the screen and placed by the software, can be, through the functions put at disposal by the programme acquired or implemented directly in the device, translated by the user in such a way as to make them come near and/or draw apart between them reciprocally.

The user, profiting from the "touch screen" of the mobile telephony device, or a pointer tool (pen or mouse), can therefore translate the two horizontal lines (A-A') and (B-B') so as to make them come near and/or draw apart reciprocally, centering well the image.

More in particular, the two horizontal lines are initially already positioned by the software automatically inside the image at a reciprocal distance in proximity of head and feet (for example, at a fixed value from the edges of the image that are statistically ok) and are subsequently positioned by dragging by the user on landmarks and that are in a not limiting example the line of the eyes and of the malleolus. The insertion of the value of h made by the user is interpreted by the programme in such a way that the final positioning made by the user of such horizontal lines, that is the distance between the two horizontal straight lines, corresponds to the height (h) inserted.

Once the two horizontal lines (A-A', B-B') has been generated, the user positions them on two landmarks that are well defined and well recognizable (for example, the line of the eyes and the line of the malleolus) and the distance between such straight lines is assumed by the programme with a value coinciding with that of the inserted height (h).

This allows not only to center the imago between the two horizontal lines to determine a value in vertical but also to cut out and eliminate, for example, the head (either for privacy questions or for simplicity of operative calculation, avoiding the "noise" that can be generated by the hair) and the feet. Both the feet and the head do not influence significantly the value calculated of the fat mass and the elimination thereof allows to simplify the digitalization of the profiles, the calculations, eliminating also from the background the pavement, which can be of a colour that disturbs the discrimination algorithms.

Moreover, head and feet are reference points, in jargon called "landmarks", easily identifiable and very well repeatable for the user, thus assuring the necessary good repetitivity of the operation.

The vertical lines (A-B, A'-B') are positioned at a reciprocal distance that in said embodiment is pre-set by the programme and is fixed preferably at a value of 0.4 h (or 0.4 times the height of the subject).

In that sense, known the height h of the subject, the width of the frame with calculation functions is pre-fixed, while, as said, the distance between the horizontal lines is adjusted by the user, preferably in such a way as to cut out head and feet, with landmarks that are easy to identify (line of the eyes and line of the malleolus) where their distance (gap) is considered by the software equal to the height of the subject inserted.

It has been found out, in fact, that such a value of 0.4 h of width of the frame allows to contain well most human profiles in all the possible variants between obese and short people and thin and tall people. Nevertheless, the distance between said vertical straight lines (A-B, A'-B') can also be fixed at different values from said value of 0.4 h or left freely traceable by the user to permit the inclusion of the sample under exam in the virtual frame.

In the preferred embodiment of the invention, said vertical lines traced between them to said value of 0.4 h, for example, and that make part of the frame of calculation inside of which the figure of the subject is contained, are generally invisible.

Further vertical lines are possibly rendered visible, also freely traceable by the user, to permit the processing of the single sample under exam in the virtual frame, thus excluding portions of background that could contain objects, shadows or disturbance colours (noise). This improves the operation of recognition and distinction between image and subject, as better clarified below.

The vertical lines, therefore, are preferably of two types, a pair is invisible and belongs to the frame of calculation in which the interaxis between the horizontal lines is assumed by the programme with proportional value of the height h of the subject. Such vertical lines, as said, are generally fixed automatically to the value of 0.4 h.

The other two vertical lines are instead visible and freely traceable by the user in such a way they touch as much as possible the body under exam to cut out and therefore eliminate as much background noise as possible.

In a variant of the invention, the translation of the horizontal lines, in theory, could also take place automatically, always with the aim of excluding, in the case of human beings, the head to preserve the privacy and in any case with an assumption of interaxis equal to the value of height h.

In all said cases, the software that is implemented directly in the mobile telephony device (or through App or because installed on it in origin) allows to define such a frame of virtual calculation, permitting a positioning and adjusting it in such a way as to contain at least in part the image of the profile acquired (or the essential part for a correct determination of the fat mass, that is all the body, preferably excluded the part of head from the eyes upwards and the feet from the ankles downwards).

Figure 3:
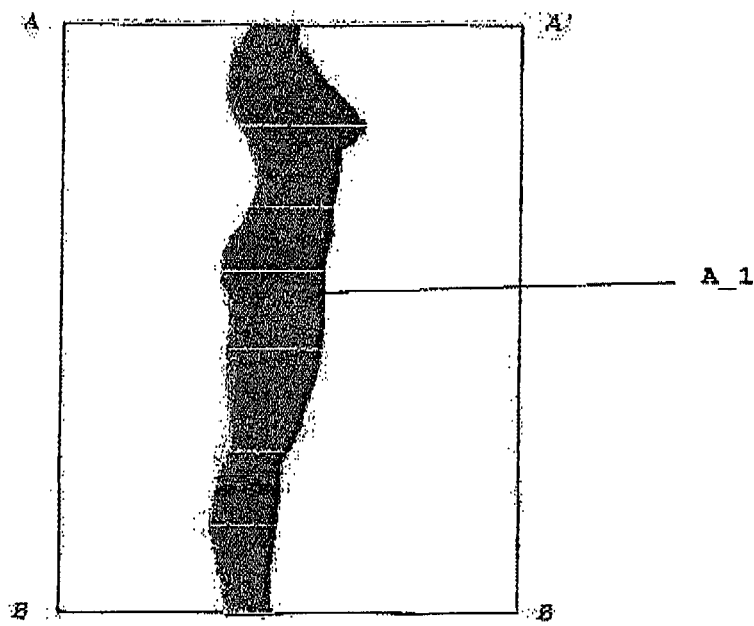
Figure 3A:
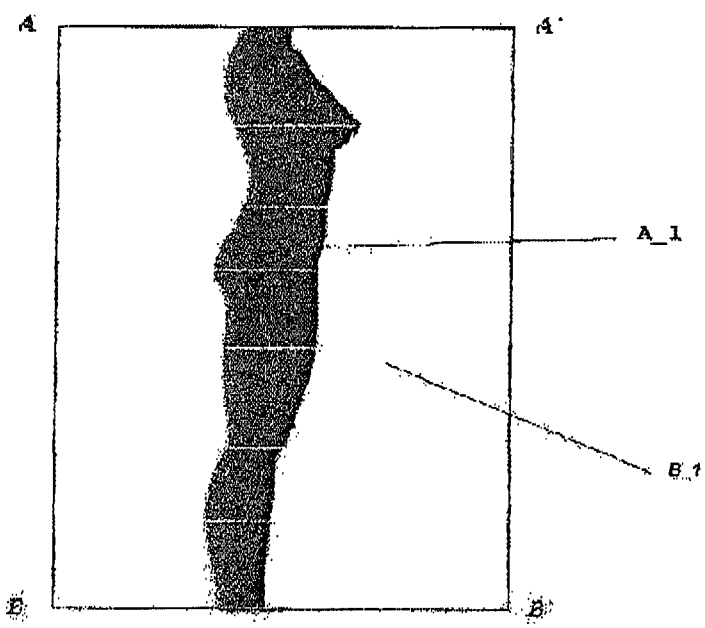
FIG. 3A shows the same image of which the area A_1 and that of the frame A_2 has been calculated.

FIG. 3 represents in an enlargened view the final result of a silhouette of profile of the subject contained in the frame, cleaned of head and feet, and of which the fat mass wants to be calculated.

The vertical lines that delimit the frame of calculation are generally not visible and are set automatically to said pre-set value, for example of 0.4 h.

At this point the software implements a calculation through the knowledge of the percentage of area (A_1) of occupation of the silhouette inside the area (B_1) of the frame, as described in detail below. Such a percentage can be obtained from the relation between the quantity at the pixels that compose the frame generated virtually and the quantity of the pixels that compose the figure (A_1), as described in detail below.

In a first phase, through a comparison of threshold of colouring and/or brightness among the pixels, the software is able to distinguish and define the image of the subject with respect to the background. In particular, the user, through for example the touch screen system already of common use in such mobile devices, is guided to touch the internal areas of the silhouette with a finger in such a way that the software acquires the information that all the pixels of a colour equal or next to those of the touched area, belong to the silhouette of the subject of which to calculate the area A_1. At this point the value of brightness of the pixels belonging to the subject "portrayed" is known and therefore the fact is known that all the pixels having such luminous intensity will belong to the figure to be examined.

An efficient alternative is that of using the number attributed at international level to the RGB (Red-Green-Blue acronym) pixels whose sum and mathematical manipulation allows to identify significant numerical variations to discriminate easily the silhouette of the body from the background, having the two surfaces colours of different RGB composition. The RGB acronym indicates said three colours, "red, green and blue", that are the three fundamental colours of the pixels from which all the other colours are created. It is known that a white background, for example, will have three RGB components of a pre-determined value, while the skin has a sum of the three components of a second pre-determined value. Being such sums or equations describing them known a priori, it is easy to do a threshold analysis to distinguish background from subject.

At this point the software implements a comparison of brightness among all the pixels contained in the frame, starting for example from the superior angle A towards the angle A' and moving line-line. All the pixels that are below or above said brightness threshold (determined in the "touch" phase of the screen on the image or with the RGB system) are kept unaltered, while the others are, for example, modified to a colour at high contrast with respect to the background, for example red ones (therefore white background and red image of profile). Alternatively, both background and image can be modified, precisely to create a still greater contrast.

In this way, a net contrast of colour between the pixels of the image "subject portrayed" and those of the background has been created.

In a new variant of the invention, once distinguished the background from the subject with two different colours in contrast, the system allows to touch up the subject, completing it with the parts that are not well recognized automatically and with the possible further artefacts, taking advantage of the touch screen and selecting from a specific "palette" or tray, the colour to interpolate (for example white if the subject is contoured with white). By simply touching the points of the screen, in the point of contact, they assume the colour selected from the "palette". In this way, the contoured image of the subject can be manually touched up and perfected. Having said that, in order to optimize such a sort of manual correction, it can be optionally foreseen to overlap or put under to the contoured image of the subject in transparency with a dimmed light also the original image of the subject that thus creates a more precise reference guide for the user to follow.

At this point, starting from a condition of background with pixels deeply different in colour with respect to the profile portrayed, the calculation of the areas A_1 e B_1 can be done, which can be for example also simply expressed by the total quantitative of the pixels that represent them, respectively.

In the embodiment in which the frame has a fixed width, the surface of such a frame is known since it is calculated as a simple geometrical calculation of base by height (it is a rectangle) and of which the base has a fixed measure (for example of 0.4 h) and the height is known since the initial value h inserted by the user is known and the height is known in proportion since the initial value h inserted by the user is known.

Even it the user draws near or moves apart reciprocally the horizontal straight lines (A-A', B-B') in order to eliminate head and feet, the software assumes the private size of the two ends equivalent to or anyway substitute of the real height furnished.

Therefore, the final, positioning of such straight lines is always assumed by the software as dimension h of the subject.

At this point the surface of the frame is known (for example in square meters, in pixels or in another equivalent unit).

For the calculation of the surface A_1 the software does not do anything but count the pixels line-line or column-column, scanning all the frame.

For instance, in a first phase it counts all the pixels of the image (therefore all the pixels that have a pre-determined value of luminous intensity, for example red).

Then it counts all the pixels of the frame by scanning line-line all the frame. As said, the frame is delimited by the two horizontal straight lines, as they have been positioned by the user in an obligatory manner (eye/ankle) and considered distanced between them in a measure equal to the height (h) shown, and those belonging to the vertical straight lines that delimit to the right and to the left the image and whose interval (distance) is preferably the fixed value of (h*0.4). Alternatively, it makes the counting by counting the pixels contained on the vertical straight line and on the horizontal straight line, to then make the multiplication.

Known the total pixels of the frame (Pixel_tot_frame) and the total pixels of the subject (Pixel_tot_1 mm) the software obtains immediately how much percentage of area (B_1) of the frame is occupied by the subject (A_1).

If, for instance, the frame is composed of 10,000 pixels and the subject foresees 3,000 pixels, then the software will obtain immediately that the subject in the image occupies ⅓ of the frame. Known the area (B_1) of the frame it is immediate to obtain the area A_1 as a percentage (33.33% in the case of the example) of the area B_1 (or in the example in question A_1=0,33333 B_1).

Known the areas (A_1) and (B_1), a specific algorithm allows to obtain the value of body volume (V_c) in accordance with the formula:

$$(V\_c)=[(A\_1)/(B\_1)]*K+C$$

where K is a corrective coefficient and C a constant.

The value of K has been determined experimentally, making a number of measurements on a sample of subjects of which the body volume is known a priori as calculated, for example, with known standard methods, such as the air plethysmography (BodPod) or the hydro-densitometry. In that manner, in a sample of subjects, standard volume measurements have been made and the same subjects have undergone to a measurement in accordance with the invention, therefore being able to interpolate a corrective or constant parameter K plus an eventual coefficient C.

Known the volume, the software can now calculate the percentage of fat mass as the relation between volume and weight of the subject, that is density with equations of the known art (Siri Equation—495/Density–450—fat percentage).

Figure 5:
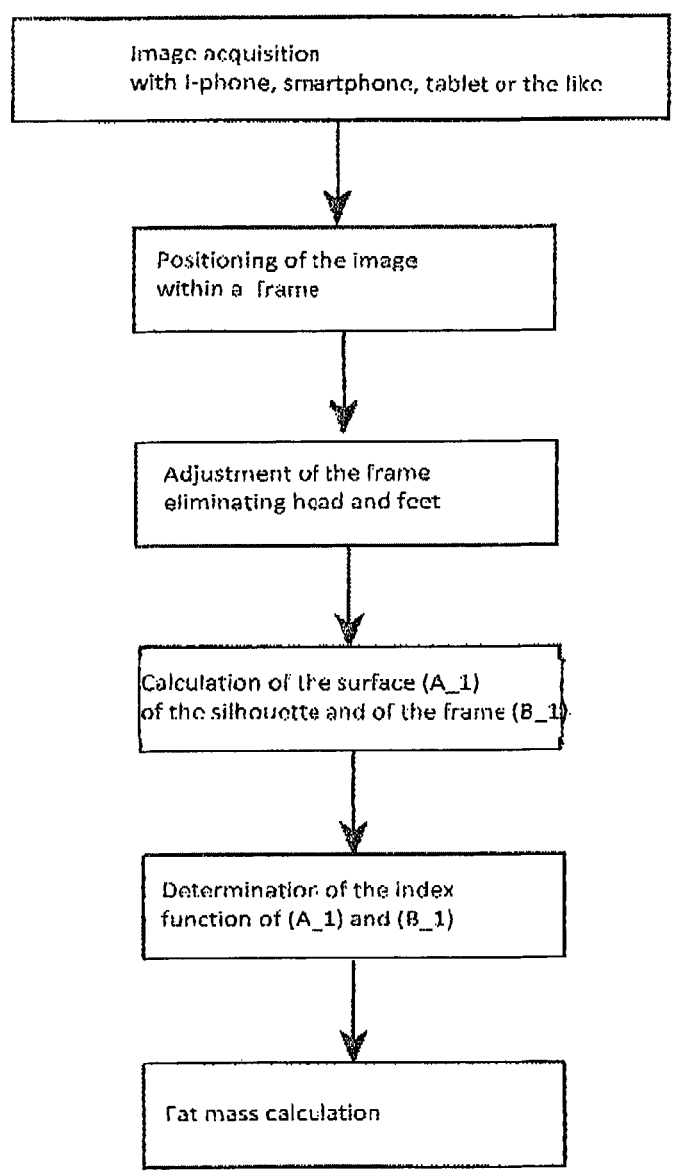
FIG. 5 shows a flowchart of the invention.

The flowchart of FIG. 5 describes in a synthetic way such a functionality.

From the formula of the volume indicated above it is nevertheless enough the knowledge of the relation between the two areas A_1 and B_1, to obtain the percentage of fat mass (FAT %). In that sense, the measurement (for example, in square meters) of the area B_1 is not indispensable but it is enough a relation between the two areas (dimensionless measurement).

That allows to realize a second embodiment of invention in which it is not indispensable to fix a priori a width of the frame at a fixed value (as said, for example, 0.4 h).

The image of the subject is separated from the frame as described before, therefore inserting the value h of the subject even if, in this case, the width can be fixed freely by the subject itself.

Having said that, the knowledge of B_1 can in fact be limited to the simple counting of the pixels contained in the frame, defining a frame made of pixels of a pre-determined colour known and moving line-line. Known all the pixels of the frame the pixels of the image that has been separated are counted as described before and said relation is obtained as the relation of number of total pixels contained in the frame and those that compose the image.

Therefore, the relation between A_1 and B_1 can be obtained also as the relation of number of pixels. This is valid for all the embodiments even if in the first one described the surface B_1 is known.

The inclusion of the datum height (h) as variable allows to obtain an idoneous estimation in association with the weight for obtaining the calculation of estimation of the percentage of fat mass.

Figure 6:
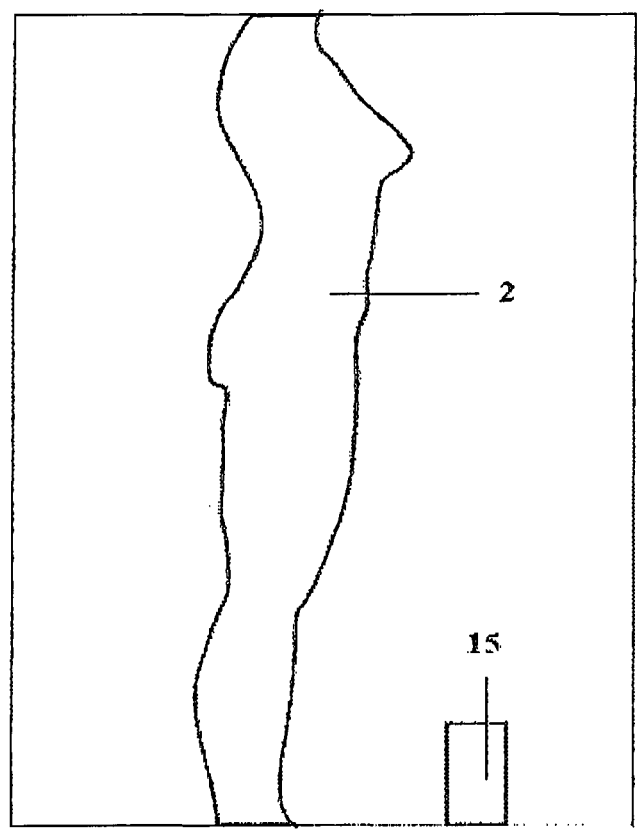
FIG. 6 shows, last, a further variant of the invention.

In a further variant, leaving as it is what has been described before, the determination of A_1 and B_1 can be clone with the help of a further object of reference included in the picture and of which the size is known, as shown in FIG. 6.

In that case, the object 15 is dimensionally known a priori and therefore counting its pixels (width, height) and counting the pixels of the frame (width, height) by proportion the values of B_1 are determined always as the multiplication of height by width. The procedure goes on by counting, as described, the pixels of the image and obtaining the percentage of the image occupied with respect to the frame and from which, known the area B_1, A_1 is also obtained.

The software can therefore foresee an option of functionality in which it is requested if it is desired to proceed through such a standard object of known size requesting, for example, in jargon, to "flag" or "Lick out" in a specific list the object (for instance, a can of drink famous worldwide), or oven more simply, a simple centimeter ruler.

FIG. 6 shows the image of profile of the subject to which an object of reference 15 is placed beside (for example, a Coca-Cola can).

In the preferred embodiment of the invention, valid for all the embodiments described it is possible to obtain directly the percentage of fat mass with algorithms deriving from statistics, for example, with analysis by linear regression obtained between the proportions of the image (A_1/B_1) and techniques of reference, like for example the X-ray densitometry (DEXA) and therefore without passing through the calculation of volume and Siri Equation, associating to the percentage of occupation some co-predictors together with the image such as age, height, sex, weight, with an equation that is typically composed as follows:

$$\text{Fat \%} = \text{constant} + (\text{age} \times K1) +/- (\text{sex} \times K2) +/- \text{weight} \times K3 +/- (\text{height} \times K4) +/- (\text{Percentage occupation} * K5)$$

For the system to work satisfactorily, as said, the acquisition of a single imago of profile is enough. It is, nevertheless, obvious that the same system functions through the use of two or more images, for example a front and a lateral one, optimizing and rendering the estimation more precise in this case.

As anticipated in the present description, such a software could be implemented inside a mobile device but, still more preferably, it is possible to foresee a specific service from a "cloud" or from a dedicated website that allows, for example, to obtain also expert advice.

In this way, the user can, for example, download the application and open it to acquire the measurement.

The image acquired and cut out in the frame is then, together with the co-predictors described, sent to the "cloud" system that gives the calculation.

The "download" of the application can require, for example, a registration of the subject to which one or more physiological and personal data are requested, which can be useful to make more precise the approximation formula that is used for said calculation of fat mass, to give nutritional advice or simply to provide a personal space in which to save and compare one's own data.

Such data can foresee, as said, the height of the subject but also the age, the weight, etc.

Figure 4:
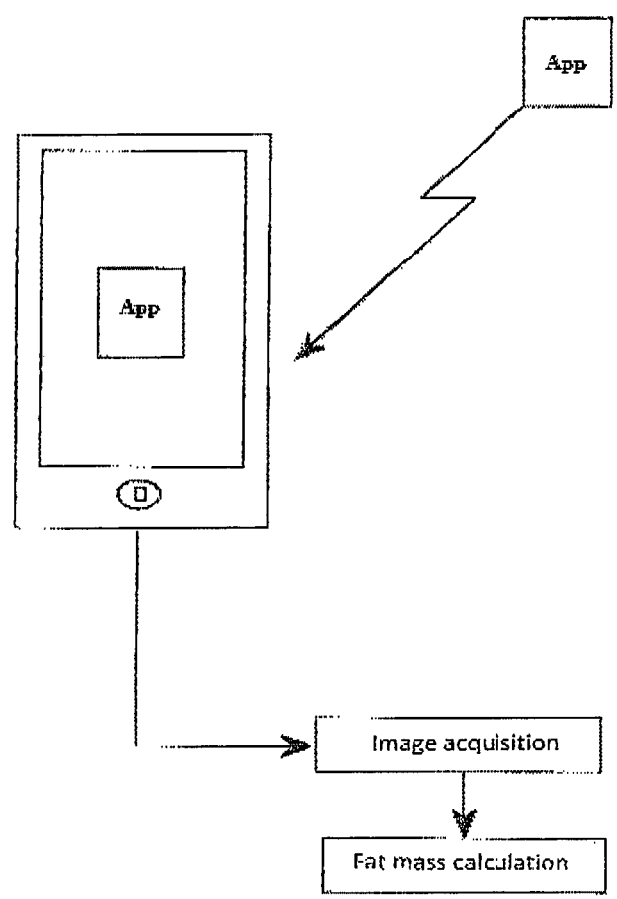
FIG. 4 shows in a schematic way a system commonly diffused for downloading an application available on the web, which is installed on an I-Phone or smartphone and that allows to acquire the image, make the necessary adjustments, conversions and calculations thereof for the body composition.

FIG. 4, in fact, shows schematically the download of the application on the mobile telephony device and its operation.

An application can be downloaded, for example, after payment, which allows to acquire the picture as described and calculate immediately the value requested or a free version of only acquisition and conditioning of the image, and in that case the data are sent to a cloud system that obtains the values of measurement only after payment of the requested sum or of a subscription fee to the service.

The present invention is viable in an identical manner not only with the mobile telephony devices capable of acquiring images and downloading applications such as I-phones and smartphones that process such images but also through similar devices such as portable devices provided with photo-camera with Wi-Fi connection, for example Tablets and the like.

For instance, "notebooks" or "Tablets", which are portable, can be used; they download applications and connect to the net through the Wi-Fi or like a mobile telephony device even if they do not allow to make calls or send messages.

As said, the present description allows to make the calculation of estimation of the content of the fat mass for subjects in general, be them animated or not and therefore human beings or animals, such as bovines, sheep, swine, mammals in general, fish products or cuts of meat for food purposes.

A thin mass can obviously be calculated, if it is desired, through the knowledge of the fat mass by a simple difference of weight.

All the eventual information deriving from knowledge of fat mass and thin mass can therefore be obtained easily with known and routine formulas.

The invention claimed is:

1. A method for determining fat mass of a subject comprising the steps of:
   acquiring at least one image containing a background and a subject (2) through a digital device (1);
   inputting at least a height value of the subject;
   generating, within the at least one image, a virtual frame (A, A', B', B) that contains at least a part of said subject (2) in the image, the virtual frame (A, A', B', B) being generated with two horizontal parallel lines (A-A', B-B') to which a value of a distance therebetween is attributed based on the inputted height (h) value of the subject, and with two vertical lines (A-B, A'-B') to which a value of distance therebetween is attributed also based on a fraction of the height (h) value of the subject,
   wherein the virtual frame (A, A', B, B') is generated through the digital device that acquires the image, wherein the horizontal lines are translatable, and
   wherein, independently from a value of translation of the horizontal lines, a value of a distance between the horizontal lines remains fixed as a reference height (h) value of the subject;
   defining an outer profile of the at least a part of said subject, said outer profile delimiting a first area (A_1), the virtual frame delimiting a second area (B_1); and
   determining a content of fat mass through an algorithm that uses at least one index which is indicative of the first area (A_1) occupied by the at least a part of the subject (2) in the virtual frame with respect to the second area (B_1) of the virtual frame.

2. The method, as per claim 1, wherein the step of determining the content further comprises a recognition step discriminating, in the virtual frame, the subject (2) of the image from the background.

3. The method, as per claim 2, wherein said recognition comprises a coloring step of pixels in the first area with a color in contrast with the background so as to distinguish the subject from the background.

4. The method, as per claim 2, wherein said recognition further comprises at choice one of the following two steps:
   determining a color of pixels belonging, respectively, to the first area and to the background, and subsequently analyzing a threshold of brightness of all the pixels contained in the virtual frame so as to distinguish the pixels belonging to the background from the pixels belonging to the first area; and
   performing an analysis based on a digital value of each pixel deriving from a sum of an RGB complex that forms the pixel.

5. The method, as per claim 2, wherein, following the recognition of the subject (2) and of the background, a counting of overall pixels of the subject and a counting of overall pixels present into the virtual frame is performed so as to obtain a percentage of the first area (A_1) with respect to the second area (B_1).

6. The method, as per claim 1, wherein the second area (B_1) of the virtual frame is calculated as a product of a width (A-A') of the frame and a height (A-B) of the frame.

7. The method, as per claim 1, wherein the first area (A_1) is calculated by multiplying a value of a percentage of first area (A_1) occupied by the image with respect to the second area of the frame (B_1) by a value of second area (B_1).

8. The method, as per claim 1, further comprising the step of sending the image to a cloud system where the fat mass is calculated.

9. The method, as per claim 1, wherein the digital device that acquires the image is selected from the group consisting of:
   a mobile telephony device configured to take pictures digitally;
   a portable notebook device with digital photo-camera or communicating with the digital photo-camera; and
   a tablet with the digital photo-camera or communicating with the digital photo-camera.

10. The method, as per claim 1, further comprising the step of inserting at least a weight (p) value of the subject.

11. The method, as per claim 1, wherein the subject is entirely arranged inside the virtual frame.

12. The method, as per claim 1, wherein at least the horizontal lines (A-A'; B-B') are visible and translatable.

* * * * *